United States Patent
Chomczynski

(10) Patent No.: US 7,812,057 B2
(45) Date of Patent: *Oct. 12, 2010

(54) COSMETIC COMPOSITIONS

(75) Inventor: Piotr Chomczynski, Cincinnati, OH (US)

(73) Assignee: Molecular Research Center, Inc., Cincinnati, OH (US)

( * ) Notice: Subject to any disclaimer, the term of this patent is extended or adjusted under 35 U.S.C. 154(b) by 824 days.

This patent is subject to a terminal disclaimer.

(21) Appl. No.: 10/925,851

(22) Filed: Aug. 25, 2004

(65) Prior Publication Data

US 2006/0045892 A1 Mar. 2, 2006

(51) Int. Cl.
*A61K 31/45* (2006.01)
(52) U.S. Cl. ..................................................... 514/729
(58) Field of Classification Search .................. 424/401
See application file for complete search history.

(56) References Cited

U.S. PATENT DOCUMENTS

| | | | |
|---|---|---|---|
| 3,987,189 A * | 10/1976 | Andree et al. ................. | 514/452 |
| 4,006,218 A * | 2/1977 | Sipos ........................... | 424/54 |
| 4,803,069 A | 2/1989 | Kekesi | |
| 5,116,605 A | 5/1992 | Alt | |
| 5,641,809 A | 6/1997 | Hagen et al. | |
| 5,654,312 A | 8/1997 | Andrulis, Jr. et al. | |
| 5,885,595 A | 3/1999 | Corey et al. | |
| 5,886,233 A | 3/1999 | Steinmeyer et al. | |
| 5,895,649 A | 4/1999 | de Lacharriere et al. | |
| 5,932,215 A | 8/1999 | de Lacharriere et al. | |
| 5,952,372 A | 9/1999 | McDaniel | |
| 5,962,517 A | 10/1999 | Murad | |
| 5,968,532 A | 10/1999 | de Lacharriere et al. | |
| 5,969,190 A | 10/1999 | Bauer et al. | |
| 5,972,892 A | 10/1999 | de Lacharriere et al. | |
| 5,972,993 A | 10/1999 | Ptchelintsev | |
| 5,994,330 A | 11/1999 | El Khoury | |
| 5,998,395 A | 12/1999 | Kligman | |
| 6,028,118 A | 2/2000 | Dupont et al. | |
| 6,054,475 A | 4/2000 | Martin et al. | |
| 6,057,341 A | 5/2000 | Charpentier | |
| 6,057,453 A | 5/2000 | Yang et al. | |
| 6,071,541 A | 6/2000 | Murad | |
| 6,071,955 A | 6/2000 | Elias et al. | |
| 6,184,422 B1 | 2/2001 | Barbier et al. | |
| 6,277,837 B1 | 8/2001 | DeLuca, Jr. et al. | |
| 6,462,075 B1 | 10/2002 | Bowen et al. | |
| 6,623,728 B2 | 9/2003 | Harichian et al. | |
| 6,645,510 B1 | 11/2003 | Coury et al. | |
| 6,660,283 B2 | 12/2003 | Breton et al. | |
| 6,692,754 B1 | 2/2004 | Makimoto et al. | |
| 6,723,755 B2 * | 4/2004 | Chomczynski ............... | 514/729 |

FOREIGN PATENT DOCUMENTS

WO WO9811882 * 3/1998

OTHER PUBLICATIONS

Stahl, Wilhelm. "Dietary tomato paste protects against ultraviolet light-induced erythema in humans." Journal of Nutrition. May 2001. 131, 5.*
Stahl, Wilhelm. Dietary Tomato Paste protects against ultraviolet light induced erythema in humans.*
Stahl, et al. Dietary Tomato Paste Protects against Ultraviolet Light-induced Erythema in humans, Journal of Nutrition, May 2001, p. 1449.*
Stahl et al. Dietary Tomato Paste Protects against ultraviolet light induced erythema in humans, Journal of Nutrition, May 2001, p. 1449.*

* cited by examiner

*Primary Examiner*—Carlos A Azpuru
*Assistant Examiner*—Melissa S Mercier
(74) *Attorney, Agent, or Firm*—Frost Brown Todd LLC

(57) ABSTRACT

A composition and method for improving skin appearance by reducing skin redness and symptoms associated with skin inflammation, irritation and skin aging by topically treating skin is disclosed. In this composition and method, an active material having the formula given below is applied to the patient at the site of said condition:

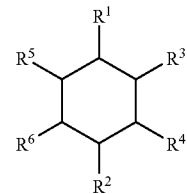

wherein $R^1$ is selected from —OH and $C_1$-$C_3$ alkyl OH; and $R^2$, $R^3$, $R^4$, $R^5$ and $R^6$ are independently selected from —H, —OH, $C_1$-$C_6$ alkyl, and $C_3$-$C_6$ cycloalkyl. The active material should contain no more than five —OH groups. Preferred active materials include 1,2-cyclohexanediol, 1,3-cyclohexanediol, 1,4-cyclohexanediol, 1,2,3-cyclohexanetriol, 1,3,5-cyclohexanetriol, and mixtures of those materials. A method of maintaining healthy hair and reducing hair loss using these actives is also disclosed.

8 Claims, No Drawings

COSMETIC COMPOSITIONS

TECHNICAL FIELD

The present invention relates to topical cosmetic compositions and methods for improving skin appearance including alleviation of redness, inflammation, irritation and skin aging, and skin imperfections associated with skin ailments, as well as for maintaining healthy skin and hair.

BACKGROUND OF THE INVENTION

Day-to-day wear and tear on the skin results in a number of conditions which can be unpleasant, uncomfortable and unsightly. These include skin redness and a variety of skin symptoms, which are associated with skin ailments such as inflammation, irritation and skin aging. The present invention provides cosmetic compositions and methods which can be used to alleviate those symptoms promoting attractiveness and/or improving skin appearance. In addition, the present invention also encompasses a cosmetic composition and method of treatment which can be used to maintain healthy skin and hair, as well as alleviate hair follicle irritation and hair loss.

Organic alcohols, diols and polyols have been disclosed for topical use in the treatment of a variety of dermatological conditions.

U.S. Pat. No. 6,290,937, Brown, et al., issued Sep. 18, 2001, and which has been withdrawn from issue by the Patent Office, described a series of pharmaceutical compositions which were said to increase the melanin content of mammalian melanocytes and which were also said to be useful for treating skin proliferative disorders, such as acne vulgaris. The compositions disclosed may utilize $C_3$-$C_{50}$ diols as the pharmaceutically active agent; 1,2-cis- and 1,2-trans-cyclohexanediol are specifically disclosed as active ingredients. In addition, 1,2-cis-cyclopentanediol was among the preferred active compounds. Since this patent has been withdrawn from issue, it does not constitute prior art.

U.S. Pat. No. 6,184,422, Barbier, et al., issued Feb. 6, 2001, discloses a group of unsaturated long-chain (for example, $C_{12}$) derivatives of cyclohexanediol. These materials are taught to be useful topically for the treatment of hyperproliferative diseases and diseases of the sebaceous glands, such as acne. See also related U.S. Pat. No. 5,969,190.

U.S. Pat. No. 5,886,233, Steinmeyer, et al., issued Mar. 23, 1999, describes cyclohexanone derivatives used to synthesize vitamin D compounds. The compounds are said to be useful for treating skin, such as in the treatment of acne.

U.S. Pat. No. 6,277,837, DeLuca, Jr., et al., issued Aug. 21, 2001, describes a group of vitamin D-related compounds which include a cyclohexanediol moiety. The compositions are taught to be useful for the treatment of cell proliferation diseases, such as psoriasis. See also related U.S. Pat. Nos. 6,127,559; 5,945,410; 5,936,133; and 5,843,928.

U.S. Pat. No. 5,641,809, Hagen, et al., issued Jun. 24, 1997, describes a skin treatment composition that includes lanolin together with an ester of a lanolin acid. The patent teaches that lanolin includes $C_9$-$C_{22}$ diols as one of its components.

U.S. Pat. No. 6,723,755, Chomczynski, issued Apr. 20, 2004, relates to the use of cyclohexanol-derived materials for the treatment of rosacea, acne vulgaris, and inflammatory symptoms. U.S. and PCT equivalents of this issued patent published as patent applications in December, 2003.

Another cyclohexane derivative, inositol, containing six hydroxyl groups, has been used in pharmaceutical and cosmetic applications. This material compound has been implicated in skin maintenance (see Daniel B. Mowrey, *The Scientific Validation of Herbal Medicine*, pp. 247-251, 1986). For example, inositol was used as an additional component in treating acne with plant extracts and erythromycin in U.S. Pat. No. 4,803,069, Kekesi, issued Feb. 7, 1989. In that patent inositol was taught, when used together with other components, to provide a normalizing effect on the skin.

U.S. Pat. No. 5,116,605, Alt, issued May 26, 1992, describes the use of inositol as an optional solubilizing and/or dispersing agent in a composition for mitigating male-pattern badness.

U.S. Pat. No. 5,962,517, Murad, issued Oct. 5, 1999, describes the use of inositol as an additional component given orally in a treatment regimen for acne using zinc compounds and vitamin A.

U.S. Pat. No. 6,645,510, Coury et al., issued Nov. 11, 2003, describes an emulsion-based skin product which may include inositol as a healing agent.

SUMMARY OF THE INVENTION

The present invention relates to a method of improving skin appearance by treating skin redness and a variety of skin symptoms which are associated with skin ailments including inflammation, irritation and skin aging, in humans, comprising topically applying to a person in need of such treatment a safe and effective amount (for example, from about 0.001 to about 10 mg/cm$^2$) of the compound having the following formula, at the site of said condition:

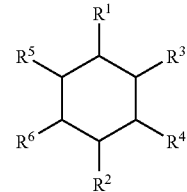

wherein $R^1$ is selected from —OH and $C_1$-$C_3$ alkyl OH (alkanols), and $R^2$, $R^3$, $R^4$, $R^5$ and $R^6$ are each independently selected from —H, —OH, $C_1$-$C_6$ alkyl and $C_3$-$C_6$ cycloalkyl; wherein the total number of —OH groups in the compound cannot exceed five.

Particularly preferred compounds are cyclohexanol, cyclohexanediols (including 1,2-cyclohexanediol, 1,3-cyclohexanediol, and 1,4-cyclohexanediol), cyclohexanetriols (including 1,2,3-cyclohexanetriol and 1,3,5-cyclohexanetriol), and mixtures of those materials. The active material may be administered with a cosmetic carrier.

The present invention also encompasses a method for maintaining healthy hair and reducing hair loss in humans comprising topically applying to the scalp of a patient in need of such treatment a safe and effective amount of the active compound defined above.

Finally, the present invention encompasses cosmetic compositions for topical application which comprise from about 0.001% to about 10% of the active compound, defined above, together with a cosmetically acceptable topical carrier. The cosmetic compositions can, for example, be in the form of a gel, cream, paste, solid, tonic, soap, body hygienic fluid, face packing jelly or shampoo.

All percentages and ratios given herein are by weight, unless otherwise specified.

All patents and other publications cited in this application are incorporated herein by reference.

DETAILED DESCRIPTION OF THE INVENTION

As used herein, the term "safe and effective amount" is intended to define that amount of active material or a cosmetic composition containing said active material which is used to provide effective treatment for the condition being treated, such as skin redness, skin inflammation, skin irritation and skin aging, or for the purpose of skin and hair maintenance, without providing the user with a significant risk of side effects that may accompany the use of any active material.

The present invention provides a composition and method of improving skin appearance by reducing skin redness or symptoms associated with skin inflammation, irritation and skin aging. This is accomplished by utilizing the topical application of an active material having the following formula:

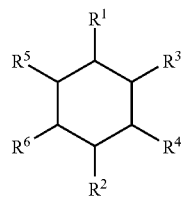

In this formula, $R^1$ is selected from —OH and $C_1$-$C_3$ alkyl OH ($C_1$-$C_3$ alkanols); and $R^2$, $R^3$, $R^4$, $R^5$ and $R^6$ are independently selected from —H, —OH, $C_1$-$C_6$ alkyl and $C_3$-$C_6$ cycloalkyl. The total number of —OH groups in the formula should not exceed five. In this formula it is preferred that $R^2$, $R^3$, $R^4$, $R^5$ and $R^6$ be selected from —H and —OH, and further that the molecule in its entirety contain no more than three hydroxyl groups. Preferred compounds for use in the present invention are selected from cyclohexanol, 2-cyclohexylethanol, cyclohexylmethanol, 3-cyclohexyl-1-propanol, 1,4-cyclohexanediol, 1,3-cyclohexanediol, 1,2-cyclohexanediol, 4-cyclohexylcyclohexanol, 4-methylcyclohexanol, 1,2,3-cyclohexanetriol, 1,3,5-cyclohexanetriol, and 1.4.5-cyclohexanetriol. Mixtures of these materials may also be used. Both the cis and trans isomers (or mixtures) of the active materials can be used herein. Isomers (both structural and stereochemical), phospho- and phosphatidylo- derivatives, and metabolites of the active compounds are intended to be included within these compound definitions.

Related materials which have been tested and found not to be useful in the present invention include cyclohexane, cyclohexene, cyclohexyl acetate, cyclohexyl chloride, 4-cyclohexyl-1-butanol, cyclohexyl carboxylic acid, 1-methylcyclohexanol, and menthol. In fact, menthol not only does not provide a benefit for use in the present invention, but it also can irritate (and thereby redden) the skin to which it is applied. Other materials which do not work in the present invention include 1,2-cyclopentanediol (both the cis and trans isomers), 5-norborene-2,2-dimethanol, and (1R,2R,3S,5S-(-))-pinanediol.

Particularly preferred compounds for use in the present invention include 1,2-cyclohexanediol, 1,3-cyclohexanediol, 1,4-cyclohexanediol, 1,3,5-cyclohexanetriol and 1,2,3-cyclohexanetriol, and mixtures of those materials. The cis and trans isomers, as well as the various optical isomers of these materials, are active in the present invention as well.

The active material is applied topically to the skin at the site to be treated (e.g., the site where there is skin redness or symptoms associated with skin ailments). The active material is typically applied to the skin in an amount of from about 0.001 to about 10 mg/cm², preferably from about 0.1 to about 1 mg/cm², more preferably from about 0.1 to about 0.5 mg/cm², but this can vary depending upon the formulation, the person and the nature of the specific skin condition being treated. The present invention can provide the user with a way to improve skin appearance by reducing skin spots and blemishes; soothing and improving irritated and inflamed skin; reducing redness, swelling and skin scars; maintaining skin texture; unplugging clogged and inflamed pores; maintaining healthy looking skin; and by maintaining healthy hair and decreasing hair loss.

The active material may be applied in combination with a cosmetic topical carrier. Topical cosmetic carriers are well known in the art and are described, for example, in U.S. Pat. No. 6,696,069, Harichian et al., issued Feb. 24, 2004; U.S. Pat. No. 6,692,754, Makimoto et al., issued Feb. 17, 2004; U.S. Pat. No. 6,660,283, Breton et al., issued Dec. 9, 2003; and U.S. Pat. No. 6,623,778, Harichian et al., issued Sep. 23, 2003; all of which are incorporated herein by reference.

When used with a topical cosmetic carrier, the active material and the topical cosmetic carrier together comprise a topical cosmetic composition. In such topical cosmetic compositions, the active material generally comprises from about 0.001% to about 10% of the composition, preferably from about 0.1% to about 10% of the composition, more preferably from about 1% to about 5% of the composition, most preferably about 1% of the composition, with the balance of the composition generally comprising the topical cosmetic carrier. Additional compatible cosmetically or therapeutically active materials, such as skin and/or hair maintenance agents, antiseptics, anti-inflammatories, depigmentation agents, allergy inhibitors, antipruritics, antiwrinkle agents, anti-hair-loss agents, herbal extracts, natural product agents, hair growth agents, sunscreens, or makeup preparations, may be included in the compositions of the present invention. The topical cosmetic carrier is a material or mixture of materials which is compatible with the active material (and supplemental active materials, if included), is non-irritating when applied to the skin, provides cosmetic benefits, and may aid penetration of the active material into the skin.

The carrier may comprise a single ingredient or a combination of two or more ingredients. Preferred cosmetic carriers comprise one or more ingredients selected from the group including water, alcohols, aloe vera gel, allantoin, glycerin, vitamin A and E oils, mineral oil, propylene glycol, polypropylene glycol-2 myristyl propionate, dimethylisosorbide, and combinations thereof Particularly preferred carriers include glycerin, propylene glycol, dimethylisosorbide, water, and mixtures of those materials.

The topical cosmetic carrier may comprise one or more ingredients selected from the group consisting of emollients, propellants, solvents, humectants, thickeners, powders and fragrances, in addition to, or instead of, the preferred topical cosmetic carrier ingredients listed above. One skilled in the art would be able to select and optimize carrier ingredients for the topical cosmetic compositions used in the present invention without undue experimentation.

If an emollient is included in the carrier, it is typically included at a level of from about 5% to about 95% of the total carrier. Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, myristyl myristate, polydimethylsiloxane, and mixtures of those material. Preferred emollients include stearyl alcohol and polydimethylsiloxane.

If a propellant is used, it is typically used at from about 5% to about 95% of the topical carrier. Suitable propellants include propane, butane, isobutane, dimethyl ether, carbon dioxide, nitrous oxide, nitrogen, and mixtures of those materials.

If a solvent is used, it is typically used at from about 5% to about 95% of the topical carrier. Suitable solvents include, for example, water, ethanol, methylene chloride, isopropanol, castor oil, ethylene glycol monoethyl ether, diethylene glycol monobutyl ether, diethylene glycol monoethyl ether, dimethyl sulfoxide, dimethyl formamide, tetrahydrofuran, glycols, including propylene glycol, and mixtures of those materials. Preferred solvents include ethyl alcohol, water, glycols, and mixtures of those materials.

If a humectant is used in the topical carrier, it is typically used at from about 5% to about 95% of the carrier. Suitable humectants include, for example, glycerin, sorbitol, sodium 2-pyrrolidone-5-carboxylate, soluble collagen, dibutyl phthalate, gelatin, panthenol, and mixtures of those materials. A preferred humectant is glycerin.

If a thickener is used in the topical carrier, it is typically used at from about 0.1% to about 95% of the carrier composition. An example of such a material is the Carbomer line of materials, comprising cross-linked acrylic acid polymers, which act in cosmetic compositions as emulsion stabilizers and viscosity adjusters, and are commercially available from Spectrum Quality Products, Gardena, Calif. The carrier composition may also include powders for the purpose of providing various desirable rheological properties to the final composition. Typically, such powder materials are used at relatively low levels, generally from about 0% to about 25% of the topical carrier. Exemplary powders include chalk, talc, fullers earth, kaolin, starch, gums, colloidal silicon dioxide, sodium polyacrylate, tetraalkylammonium smectites, trialkylaryl smectites, chemically modified magnesium aluminum silicate, organically-modified montmorillonite clay, hydrated aluminum silicate, fumed silica, carboxyvinyl polymer, sodium carboxymethyl cellulose, ethylene glycol monostearate, and mixtures of those materials. If a fragrance is included in the topical carrier, it is typically used at from about 0.001% to about 0.5% of the carrier. Colorants (dyes, pigments) may also be included at their art-established levels if the cosmetic composition to be formulated is a color cosmetic.

Waxes may also be included in the topical carrier, primarily for their ability to provide desirable rheological properties, such as viscosity, to the carrier, Examples of suitable waxes include animal waxes, vegetable waxes, mineral waxes, various fractions of natural waxes, synthetic waxes, petroleum waxes, ethylenic polymers, hydrocarbon types such as Fischer-Tropsch waxes, silicone waxes and mixtures of such materials having a melting point between about 40° C. and 100° C.

Techniques for formulating topical carriers which may be used in the present invention, as well as components included in those carriers, are described in the following references: *Modern Pharmaceutics*, Chapters 9 and 10, Banker & Rhodes, eds. (1979); Lieberman et al., *Pharmaceutical Dosage Forms* (1981); and Ansel, *Introduction to Pharmaceutical Dosage Forms*, $2^{nd}$ edition, (1976); *International Cosmetic Ingredient Dictionary, Tenth edition*, (2004), published by Cosmetic, Toiletry and Fragrance Association, all incorporated herein by reference. Topical cosmetic compositions that can be applied locally to the skin may be in any form including solutions, oils, creams, ointments, gels, lotions, sprays, skin patches, and the like.

The active material used in the present invention may be supplemented with cosmetic and/or pharmaceutically active materials and herbal extracts, known in the art, to provide further benefits to the user. These cosmetic and pharmaceutical compounds may comprise, for example, vitamins, steroids, non-steroidal anti-inflammatory compounds, retinoids, antibiotics and other antibacterial agents, antifungal agents, antioxidants, herbal extracts and natural product extracts. Examples of specific materials include vitamin C, vitamin K, vitamin B, benzoyl peroxide, lycopene, inositol, erythromycin, minoxidil, zinc oxide, retinol, panthenol, tretinoin, keratin, hydrolyzed wheat proteins, green tea extract, garlic extract, and mixtures thereof. These compounds have diverse effects on skin and/or hair. However, none of them is used as a complete substitute for the active compounds of the present invention. The materials given orally or as a part of the composition of the present invention can potentiate or complement the active compounds of the present invention either as a part of a single composition or taken orally as a supplement to a composition/method of the present invention. An oral supplement in the present invention can be taken daily or every 2-3 days. An especially safe and useful oral supplement in the present invention is a processed tomato product selected from tomato juice, homogenate, condensate, paste, extracts, extracted products, and mixtures thereof. For example, a supplement to the topical application in this invention may comprise a daily oral dose of 200 ml of tomato juice. Tomato products can be further fortified with vitamins or other cosmetic or pharmaceutical supplements beneficial in the treatment of the present invention. Tomato products extracted with water retain their activity in the present invention. This indicates that their active ingredients(s) is water insoluble.

The present invention also relates to a method for maintaining healthy hair and reducing hair loss in humans comprising the topical application to the scalp of a patient in need of such treatment of a safe and effective amount of a compound selected from the active materials having the formula described above. Generally, the active material is applied in an amount of from about 0.001 to about 10 mg/cm$^2$, preferably from about 0.1 to about 0.5 mg/cm$^2$. The active materials may be used in combination with a topical cosmetic carrier such as those described above; shampoos, hair conditioners, hair sprays, and hair mousses are particularly suitable vehicles. Stereoisomers and optical isomers of the active materials may be used.

The present invention also relates to topical cosmetic compositions which may be used in the treatment methods defined in this application. Those compositions comprise: from about 0.001% to about 10%, preferably from about 0.5% to about 10%, more preferably from about 1% to about 5%, most preferably about 1%, of an active material having the formula;

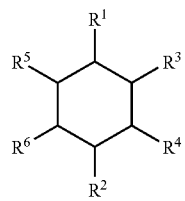

wherein $R^1$ is selected from —OH and $C_1$-$C_3$ alkyl OH (alkanols); and $R^2$, $R^3$, $R^4$, $R^5$ and $R^6$ are each independently selected from —H, —OH, $C_1$-$C_6$ alkyl and $C_3$-$C_6$ cycloalkyl, provided that the active material contains no more than five —OH groups; the balance of the composition being a topical cosmetic carrier, as defined above.

Preferred active materials include cyclohexanol, 2-cyclohexylethanol, cyclohexylmethanol, 3-cyclohexyl-1-propanol, 1,4-cyclohexanediol, 1,3-cyclohexanediol, 1,2-cyclohexanediol, 4-cyclohexylcyclohexanol, 4-methylcyclohexanol, 1,2,3-cyclohexanetriol, 1,3,5-cyclohexanetriol, 1,4,5-cyclohexanetriol, and mixtures thereof. Both the cis and trans isomers and optical isomers of those materials may be used. Particularly preferred materials include 1,2-cyclohexanediol, 1,3-cyclohexanediol, 1,4-cyclohexanediol, 1,2,3-cyclohexanetriol, 1,3,5-cyclohexanetriol, and mixtures thereof.

The compositions of the present invention can be formulated in any conventional manner including, for example, gel, cream, paste, solid, tonic, soap, body hygienic fluid, face packing jelly or shampoo.

EXAMPLE 1

A cosmetic composition of the present invention, having the formulation set forth in the following table, is made as follows: Carbomer 940, 5 g; 1,4-cyclohexanediol, 10 g; and glycerin, 3 g were mixed with 982 g water. The resulting gel was adjusted with sodium hydroxide to pH 7.0, to further thicken the gel. An aliquot of about 0.01 ml of the composition was applied per 1 cm² of facial skin 2-3 times per day and provided improvement in the skin appearance and relief to skin irritation and skin inflammation symptoms.

| Component | % (by weight) |
| --- | --- |
| Carbomer 940 (Spectrum Quality Products, Inc.) | 0.5 |
| glycerin | 0.3 |
| 1,4-cyclohexanediol (cis/trans) | 1.0 |
| sodium hydroxide | sufficient to adjust composition to pH = 7.0 |
| water | balance |

Carbopol 940 (Noveon, Inc., Cleveland, Ohio) may be substituted for the Carbomer, in whole or in part.

EXAMPLE 2

A cosmetic composition of the present invention is made by mixing the following ingredients with 981 g water:

| | |
| --- | --- |
| Carbomer 940 | 5 g |
| 1,2,3-cyclohexanetriol (cis/trans) | 10 g |
| glycerin | 1 g |
| inositol | 2 g |
| methylparabenzene | 1 g |

The resulting gel is adjusted to pH 7.0 with sodium hydroxide to further thicken the gel. An aliquot of the formula is hand-applied on facial and neck skin 2-3 times a day and provides the benefits described herein.

EXAMPLE 3

A cosmetic composition of the present invention is made by mixing the following ingredients with 984 g water:

| | |
| --- | --- |
| Carbomer 940 | 5 g |
| 1,4-cyclohexanediol (trans) | 10 g |
| propylene glycol 200 | 1 g |

The resulting gel is adjusted to pH 7.0 with sodium hydroxide to further thicken the gel. An aliquot of the formula is hand-applied on facial skin 2-3 times a day and provides the benefits described herein.

EXAMPLE 4

A cosmetic composition of the present invention is made by mixing the following ingredients with 985.2 g water:

| | |
| --- | --- |
| Carbomer 940 | 5 g |
| 1,3-cyclohexanediol (cis/trans) | 4 g |
| 1,4-cyclohexanediol (cis/trans) | 4 g |
| glycerin | 1 g |
| *aloe* extract (powder, Spectrum Quality Products) | 0.5 g |
| garlic extract (powder, Spectrum Quality Products) | 0.3 g |

The resulting gel is adjusted to pH 7.0 with sodium hydroxide to further thicken the gel. An aliquot of the gel is hand-applied to facial skin and forearm skin 1-3 times a day and provides the benefits described herein.

EXAMPLE 5

A cosmetic composition of the present invention is made by dissolving the following ingredients in 998 g water:

| | |
| --- | --- |
| 1,4-cyclohexanediol (cis/trans) | 0.5 g |
| 1,2,3-cyclohexanetriol (cis/trans) | 0.5 g |
| glycerin | 1 g |

A 10 ml aliquot of the solution is poured into a 15 ml drop bottle and the solution is applied to the patient's scalp once a day. Hair follicle irritation and hair loss is reduced.

What is claimed is:
1. A method of maintaining healthy skin and skin appearance in humans by achieving effects selected from reducing skin spots and blemishes; soothing irritated skin; reducing redness, swelling and skin scars; maintaining skin texture; unplugging clogged and inflamed pores; and combinations thereof, comprising topically applying to a person in need of such treatment a composition consisting essentially of a safe and effective amount of an active material in the form of a cis/trans isomer mixture, selected from 1,4-cyclohexanediol, 1,3 cyclohexanediol, 1,2-cyclohexanediol, 1,2,3-cyclohexanetriol, 1,3,5-cyclohexanetriol, and mixtures thereof.

2. The method according to claim 1 wherein the active material is applied to the skin in an amount of from about 0.001 to about 10 mg/cm$^2$.

3. The method according to claim 2 wherein the composition additionally includes a topical cosmetic carrier.

4. The method according to claim 3 wherein the cosmetic carrier comprises a material selected from propylene glycol, glycerin, water, dimethylisosorbide, and mixtures thereof.

5. The method according to claim 3 wherein the carrier is formulated in a composition selected from solutions, suspensions, gels, pastes, solids and soaps.

6. The method according to claim 1 wherein the active material is selected from 1,2-cyclohexanediol, 1,3-cyclohexanediol, 1,4-cyclohexanediol, and mixtures thereof.

7. A method of maintaining healthy skin and skin appearance in humans by achieving effects selected from reducing skin spots and blemishes; soothing irritated skin;
reducing redness, swelling and skin scars; maintaining skin texture; unplugging clogged and inflamed pores; and combinations thereof, comprising (a) topically applying to a person in need of such treatment a composition consisting essentially of a safe and effective amount of an active material in the form of a cis/trans isomer mixture, selected from 1,4-cyclohexanediol, 1,3-cyclohexanediol, 1,2-cyclohexanediol, 1,2,3-cyclohexanetriol, 1,3,5-cyclohexanetriol, and mixtures thereof, and (b) orally administering to said person a medically active oral supplement.

8. The method of claim 7 where the oral supplement is a tomato product selected from juice, homogenate, condensate, paste, extracts, extracted products, and mixtures thereof.

* * * * *